(12) United States Patent
Grosman et al.

(10) Patent No.: US 11,896,370 B2
(45) Date of Patent: *Feb. 13, 2024

(54) METHOD AND/OR SYSTEM FOR ASSESSING A PATIENT'S GLYCEMIC RESPONSE

(71) Applicant: Medtronic MiniMed, Inc., Northridge, CA (US)

(72) Inventors: Benyamin Grosman, North Hollywood, CA (US); Francine R. Kaufman, Los Angeles, CA (US); Desmond Barry Keenan, Hollywood, CA (US); Anirban Roy, Calabasas, CA (US)

(73) Assignee: Medtronic MiniMed, Inc., Northridge (CA)

( * ) Notice: Subject to any disclaimer, the term of this patent is extended or adjusted under 35 U.S.C. 154(b) by 845 days.

This patent is subject to a terminal disclaimer.

(21) Appl. No.: 16/886,618

(22) Filed: May 28, 2020

(65) Prior Publication Data
US 2020/0289037 A1 Sep. 17, 2020

Related U.S. Application Data

(63) Continuation of application No. 13/715,408, filed on Dec. 14, 2012, now Pat. No. 10,694,983.
(Continued)

(51) Int. Cl.
*A61B 5/145* (2006.01)
*A61B 5/00* (2006.01)
(Continued)

(52) U.S. Cl.
CPC ........ *A61B 5/14532* (2013.01); *A61B 5/1473* (2013.01); *A61B 5/4839* (2013.01); *A61B 5/4866* (2013.01); *A61B 5/7275* (2013.01); *A61M 5/142* (2013.01); *G16H 20/17* (2018.01); *G16H 50/20* (2018.01); *A61B 5/1451* (2013.01); *A61B 5/6849* (2013.01)

(58) Field of Classification Search
CPC .......... A61M 5/1723; A61M 2230/201; A61B 5/14532
See application file for complete search history.

(56) References Cited

U.S. PATENT DOCUMENTS 7,833,157 B2 11/2010 Gottlieb et al.
10,694,983 B2 6/2020 Grosman et al.
(Continued)

OTHER PUBLICATIONS

Percival MW, Bevier WC, Wang Y, et al. Modeling the Effects of Subcutaneous Insulin Administration and Carbohydrate Consumption on Blood Glucose. Journal of Diabetes Science and Technology. 2010;4(5):1214-1228 (Year: 2010).*
(Continued)

*Primary Examiner* — Tse W Chen
*Assistant Examiner* — Michael A Catina
(74) *Attorney, Agent, or Firm* — Weaver Austin Villeneuve & Sampson LLP

(57) ABSTRACT

Subject matter disclosed herein relates to a method and/or system for tailoring insulin therapies to physiological characteristics of a patient. In particular, observations of a blood glucose concentration of a patient responsive to a meal profile and an insulin profile may be used for estimating one or more physiological parameters.

20 Claims, 8 Drawing Sheets

Related U.S. Application Data

(60) Provisional application No. 61/588,348, filed on Jan. 19, 2012, provisional application No. 61/588,340, filed on Jan. 19, 2012.

(51) Int. Cl.
   *A61M 5/142* (2006.01)
   *A61B 5/1473* (2006.01)
   *G16H 20/17* (2018.01)
   *G16H 50/20* (2018.01)

(56) References Cited

U.S. PATENT DOCUMENTS

| | | |
|---|---|---|
| 2004/0043106 A1 | 3/2004 | Anfinsen et al. |
| 2008/0183060 A1 | 7/2008 | Steil et al. |
| 2011/0313390 A1 | 12/2011 | Roy et al. |
| 2013/0190583 A1 | 7/2013 | Grosman et al. |

OTHER PUBLICATIONS

Berghe, et. al. "Intensive insulin therapy in critically ill patients," The New England Journal of Medicine, vol. 345, Nov. 8, 2001, 9 pgs.

Steil, et. al., "The Effect of Insulin Feedback on Closed Loop Glucose Control", J Clin Endocrinol Metab May 2011;96(5): 1402-8. doi: 10.1210/jc.2010-2578. Epub Mar. 2, 2011, 7 pgs.

Kaufman, "Type 1 Diabetes Mellitus", Pediatrics in Review, American Academy of Pediatrics, Sep. 2003; 10 pgs. 291-300.

Prosecution History from U.S. Appl. No. 13/715,408, dated Jul. 17, 2015 through Jun. 10, 2020, 294 pp.

U.S. Advisory Action dated Aug. 20, 2019, in U.S. Appl. No. 13/715,408.

U.S. Advisory Action dated Aug. 22, 2017, in U.S. Appl. No. 13/715,408.

U.S. Final Office Action dated Jun. 14, 2018, in U.S. Appl. No. 13/715,408.

U.S. Final Office Action dated Mar. 11, 2019, in U.S. Appl. No. 13/715,408.

U.S. Final Office Action dated May 17, 2017, in U.S. Appl. No. 13/715,408.

U.S. Non-Final Office Action dated Jan. 14, 2016, in U.S. Appl. No. 13/715,408.

U.S. Non-Final Office Action dated May 9, 2016, in U.S. Appl. No. 13/715,408.

U.S. Non-Final Office Action dated Nov. 2, 2016, in U.S. Appl. No. 13/715,408.

U.S. Non-Final Office Action dated Nov. 15, 2017, in U.S. Appl. No. 13/715,408.

U.S. Non-Final Office Action dated Oct. 10, 2018, in U.S. Appl. No. 13/715,408.

U.S. Non-Final Office Action dated Sep. 26, 2019, in U.S. Appl. No. 13/715,408.

U.S. Notice of Allowance dated Feb. 25, 2020, in U.S. Appl. No. 13/715,408.

* cited by examiner

METHOD AND/OR SYSTEM FOR ASSESSING A PATIENT'S GLYCEMIC RESPONSE

This application is a continuation of, and claims the benefit of priority from, U.S. patent application Ser. No. 13/715,408, entitled "Method and/or System For Assessing a Patient's Glycemic Response," filed Dec. 14, 2012, which in turn claims the benefit of priority to U.S. Provisional Patent Appl. Nos. 61/588,340 titled "Model Based Insulin Therapy," filed on Jan. 19, 2012 and 61/588,348 titled "Improved System to Regulate Glycemia," filed on Jan. 19, 2012, all of which such applications are assigned to the assignee of claimed subject matter, and all of which such applications are incorporated herein by reference in their entirety, for all purposes.

BACKGROUND

1. Field

Subject matter disclosed herein relates to monitoring and/or controlling blood glucose levels in patients.

2. Information

The pancreas of a normal healthy person produces and releases insulin into the blood stream in response to elevated blood plasma glucose levels. Beta cells (β-cells), which reside in the pancreas, produce and secrete insulin into the blood stream as it is needed. If β-cells become incapacitated or die, a condition known as Type 1 diabetes mellitus (or in some cases, if β-cells produce insufficient quantities of insulin, a condition known as Type 2 diabetes), then insulin may be provided to a body from another source to maintain life or health.

Traditionally, because insulin cannot be taken orally, insulin has been injected with a syringe. More recently, the use of infusion pump therapy has been increasing in a number of medical situations, including for delivering insulin to diabetic individuals. For example, external infusion pumps may be worn on a belt, in a pocket, or the like, and they can deliver insulin into a body via an infusion tube with a percutaneous needle or a cannula placed in subcutaneous tissue.

As of 1995, less than 5% of Type 1 diabetic individuals in the United States were using infusion pump therapy. Presently, over 7% of the more than 900,000 Type 1 diabetic individuals in the U.S. are using infusion pump therapy. The percentage of Type 1 diabetic individuals that use an infusion pump is growing at a rate of over 2% each year. Moreover, the number of Type 2 diabetic individuals is growing at 3% or more per year, and growing numbers of insulin-using Type 2 diabetic individuals are also adopting infusion pumps. Additionally, physicians have recognized that continuous infusion can provide greater control of a diabetic individual's condition, so they too are increasingly prescribing it for patients.

A closed-loop infusion pump system may include an infusion pump that is automatically and/or semi-automatically controlled to infuse insulin into a patient. The infusion of insulin may be controlled to occur at times and in amounts that are based, for example, on blood glucose measurements obtained from an embedded glucose sensor in real-time. Closed-loop infusion pump systems may also employ the delivery of glucose and/or glucagon, in addition to the delivery of insulin, for controlling blood-glucose levels of a patient (e.g., in a hypoglycemic context).

SUMMARY

Briefly, example embodiments may relate to methods, systems, apparatuses, and/or articles, etc. for determining a meal profile of a patient indicative of an ingestion of a carbohydrate; determining an insulin profile of the patient indicative of insulin infused by the patient; obtaining one or more observations of a blood glucose concentration of said patient responsive to the meal profile and said insulin profile; and estimating one or more physiological parameters of the patient to model the blood glucose concentration based, at least in part, on the meal profile, the insulin profile and the one or more observations of said blood glucose concentration. At least one of the one or more physiological parameters may comprise a blood glucose concentration observed following a fasting period during an infusion of insulin to the patient at a constant basal rate. In a particular implementation, the meal profile may comprise a multi-component expression. For example, the meal profile may be defined by multiple humps. In another implementation, the insulin profile may comprise an expression of subcutaneous insulin and an expression of insulin infused. Here, for example, the insulin profile may be defined, at least in part, according to a pharmacokinetic model.

In one particular application, at least one of the estimated parameters may be applied in determining a meal bolus or a correction bolus. In another particular application, at least one of the estimated parameters may be applied in determining limits to an amount of insulin to be specified in an insulin pump command. In another particular application, at least one of the estimated parameters may be applied in tuning parameters of a controller to determine an amount of insulin to be infused to a patient on discrete command intervals. In yet another particular implementation, an insulin infusion basal rate for the patient may be computed based, at least in part, on at least one of the estimated physiological parameters.

In another implementation, an apparatus comprises: a special purpose computing apparatus to: determine a meal profile of a patient indicative of an ingestion of a carbohydrate; determine an insulin profile of the patient indicative of insulin infused by the patient; obtain one or more observations of a blood glucose concentration of the patient responsive to the meal profile and said insulin profile; and estimate one or more physiological parameters of the patient to model said blood glucose concentration based, at least in part, on the meal profile, the insulin profile and the one or more observations of the blood glucose concentration. In a particular implementation, at least one of the one or more physiological parameters comprises a blood glucose concentration observed following a fasting period during an infusion of insulin to the patient at a constant basal rate.

In one particular implementation, the meal profile comprises a multi-component expression. For example, the meal profile may be defined, at least in part, by multiple humps. In another particular implementation, the insulin profile may comprise an expression of subcutaneous insulin and an expression of insulin infused. In a particular example, the insulin profile may be defined, at least in part, according to a pharmacokinetic model.

In a particular application, the special purpose computing apparatus may apply at least one of the estimated parameters in determining a meal bolus or a correction bolus. In another particular application, the special purpose computing apparatus may further to apply at least one of the estimated parameters in determining limits to an amount of insulin to be specified in an insulin pump command. In yet another particular application, the special purpose computing apparatus may further apply at least one of the estimated parameters to tune parameters of a controller to determine an amount of insulin to be infused to a patient on discrete command intervals. In yet another particular application, implementation, the special purpose computing apparatus may compute an insulin infusion basal rate for the patient based, at least in part, on at least one of the one or more physiological parameters.

In a particular implementation, the apparatus may further comprise a continuous glucose monitoring device to provide the one or more observations of the blood glucose concentration based, at least in part, on signals generated by a glucose sensors. In another particular implementation, the apparatus may further comprise an insulin infusion pump to receive commands from the special purpose computing apparatus determined based, at least in part, on the estimated one or more physiological parameters.

In another implementation, an article may comprise a storage medium comprising machine-readable instructions stored thereon which are executable by a special purpose computing apparatus to: determine a meal profile of a patient indicative of an ingestion of a carbohydrate; determine an insulin profile of the patient indicative of insulin infused by the patient; obtain one or more observations of a blood glucose concentration of the patient responsive to the meal profile and said insulin profile; and estimate one or more physiological parameters of the patient to model said blood glucose concentration based, at least in part, on the meal profile, the insulin profile and the one or more observations of the blood glucose concentration.

In yet another implementation, an apparatus may comprise: means for determining a meal profile of a patient indicative of an ingestion of a carbohydrate; means for determining an insulin profile of the patient indicative of insulin infused by the patient; means for obtaining one or more observations of a blood glucose concentration of said patient responsive to the meal profile and the insulin profile; and means for estimating one or more physiological parameters of the patient to model the blood glucose concentration based, at least in part, on the meal profile, the insulin profile and the one or more observations of the blood glucose concentration.

Other alternative example embodiments are described herein and/or illustrated in the accompanying Drawings. Additionally, particular example embodiments may be directed to an article comprising a storage medium including machine-readable instructions stored thereon which, if executed by a special purpose computing device and/or processor, may be directed to enable the special purpose computing device/processor to execute at least a portion of described method(s) according to one or more particular implementations. In other particular example embodiments, a sensor may be adapted to generate one or more signals responsive to a measured blood glucose concentration in a body while a special purpose computing device/processor may be adapted to perform at least a portion of described method(s) according to one or more particular implementations based upon one or more signals generated by the sensor.

BRIEF DESCRIPTION OF THE FIGURES

Non-limiting and non-exhaustive features will be described with reference to the following figures, wherein like reference numerals refer to like parts throughout the various figures.

DETAILED DESCRIPTION

Figure 1:
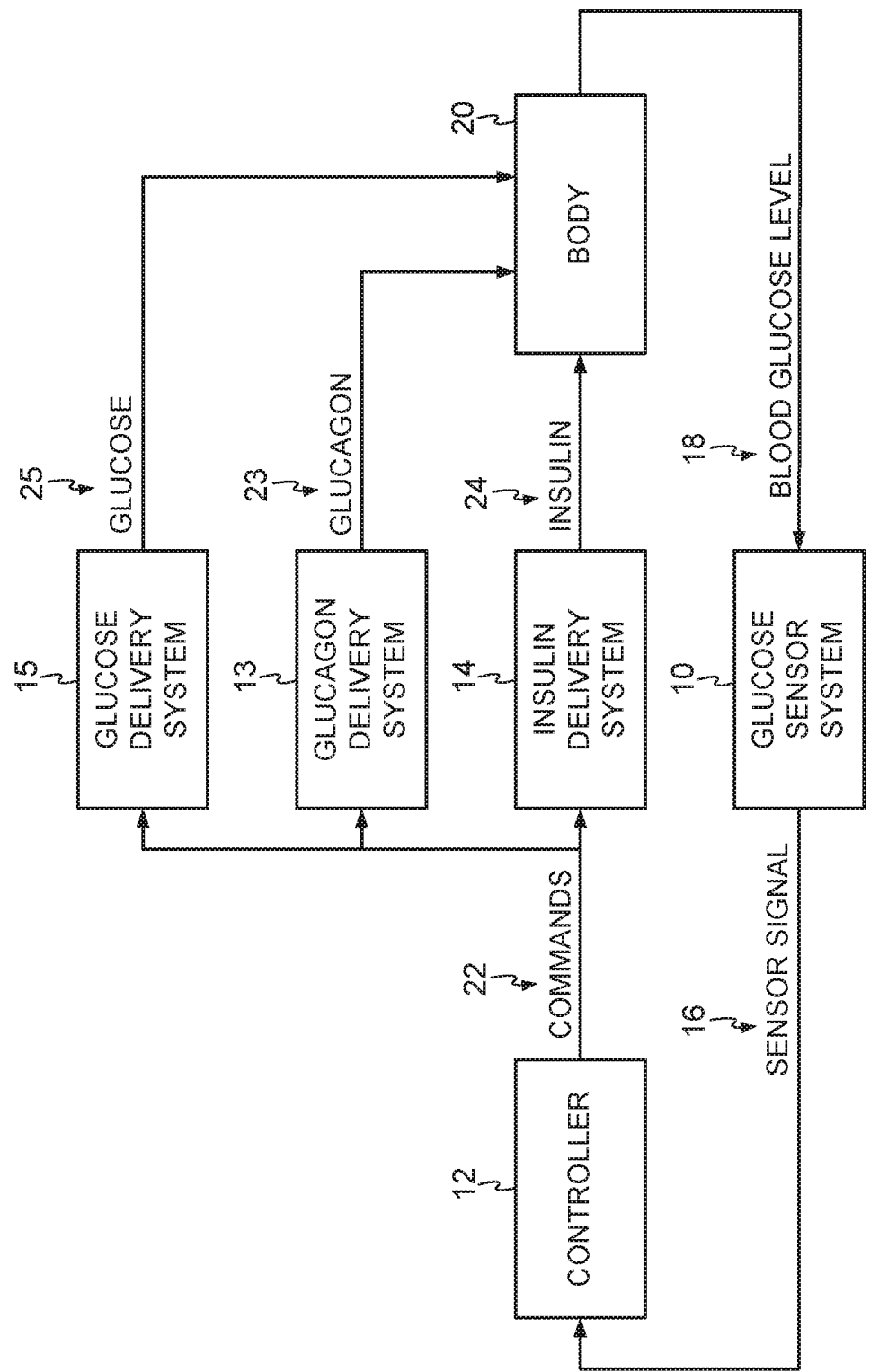
FIG. 1 is a block diagram of an example closed loop glucose control system in accordance with an embodiment.

In an example glucose control system environment, blood-glucose measurements may be employed in a closed loop infusion system for regulating a rate of fluid infusion into a body. In particular example embodiments, a control system may be adapted to regulate a rate of insulin, glucagon, and/or glucose infusion into a body of a patient based, at least in part, on a glucose concentration measurement taken from a body (e.g., from a glucose sensor and/or metered blood glucose measurement). In certain example implementations, such a system may be designed to model a pancreatic beta cell (β-cell). Here, such a system may enable a patient to control an infusion device for releasing insulin or glucagon into the patient's body for effective blood glucose management. Here, such a system may be adapted to control infusion of insulin and/or glucagon so as to control/maintain a patient's blood glucose within a target range, thus reducing the risk that a patient's blood glucose level transitions to dangerous extreme levels in the absence of patient action.

According to certain embodiments, examples of closed-loop systems as described herein may be implemented in a hospital environment to monitor and/or control levels of glucose in a patient. Alternatively, according to certain embodiments, examples of closed-loop systems as described herein may be implemented in non-hospital environments to monitor and/or control levels of glucose in a patient. Here, a patient or other non-medical professional may be responsible for interacting with a closed-loop system.

To maintain healthy glucose levels, a person with type 1 diabetes may manage their glycemia by monitoring blood glucose levels, controlling diet, exercise, and self-administering appropriate amounts of insulin at appropriate times. Deviations from such glycemic management, such as skipping an insulin bolus at meal time or underestimating the carbohydrate content of a meal may bring about prolonged hyperglycemia. Likewise, receiving too much insulin (e.g., by over-bolusing) for a given blood glucose level and/or meal may bring about severe hypoglycemia. Other external factors, such as exercise or stress, may also contribute to glycemic deviations.

In a particular embodiment of a closed-loop system, such a system may be adapted to control infusion of insulin and/or glucagon so as to control/maintain a patient's blood glucose within a target range, thus reducing the risk that a patient's blood glucose level transition to dangerous extreme levels. Again, such a mechanism may reduce the risk of hypoglycemia and hyperglycemia if a patient, non-medical professional or medical professional is not fully attentive to providing inputs to the system for effective glycemic management.

According to an embodiment, depending on a patient's particular physiology, a target or set-point glucose level may be established. For example, such a target or set-point glucose level may be defined based, at least in part, on guidelines established by the American Diabetes Association (ADA) and/or clinical judgment of a patient's physician. Here, for example, the ADA has recommended a pre-prandial blood glucose concentration of between 80-130 mg/dl, which is in the normal glycemic range. Alternatively, target or set-point glucose level may be fixed at 120 mg/dl. In yet another alternative, a target or set-point blood glucose concentration may vary over time depending on particular patient conditions. It should be understood, however, that these are merely examples of a target or set-point blood glucose concentration, and claimed subject matter is not limited in this respect.

According to an embodiment, a closed-loop system may be employed to maintain a patient's glucose level in a range about a predetermined set-point or target level as described in U.S. patent application Ser. No. 12/820,944, filed on Jun. 22, 2010, and assigned to the assignee of claimed subject matter. Here, insulin may be infused to the patient at a predetermined basal rate while the patient's glucose level is within the predetermined range. If the glucose level escapes that range, a different infusion rate may be applied based, at least in part, on the predetermined set-point or target level. For example, if the patient's glucose level exceeds the range, an infusion rate may be increased. In another example, if the patient's glucose level falls below a particular level, an insulin infusion rate may be reduced from the predetermined basal rate. Of course, these are merely examples of how the insulin infusion rate may be changed if a patient's glucose level escapes a particular range, and claimed subject matter is not limited in this respect.

By maintaining a predetermined basal insulin infusion rate while the glucose level is within a target range, extreme glycemic variations may be reduced or avoided altogether. This may provide a patient with improved glycemic control in circumstances in which they would otherwise be exposed to undesirable extremes of glycemia. Here, while such a patient may remain in control of insulin infusion decisions, particular embodiments may respond automatically in the absence of particular patient action (e.g., forgetting to bolus insulin to cover a meal) to prevent blood glucose from reaching extreme levels.

A controller may employ any one of several control techniques algorithms for computing determining commands for a pump in attempt to maintain a patient's observed blood glucose concentration within a target range. For example, a controller may employ a proportional-integral-derivative (PID) control algorithm in conjunction with controlling a patient's blood glucose level within a particular range as described in U.S. patent application Ser. No. 12/820,944, filed on Jun. 22, 2010, and assigned to the assignee of claimed subject matter. Here, such a PID algorithm may, at least in part, predict a level of blood glucose in a patient at some time in the future and, based on such a prediction, compute commands to be provided to an infusion pump.

Current PID algorithms typically have limited ability to be tailored to specific characteristics of a patient. While current PID algorithms may effectively respond to sensor measurement errors or some patient specific characteristics, current PID algorithms do not necessarily fully address patient specific characteristics, and much work remains to be done in this area.

Briefly, a profile of a patient's meal may be characterized, at least in part, by carbohydrate content. A profile of external insulin infused by the patient may also be characterized. One or more of the patient's physiological parameters may then be estimated based, at least in part, on the patient's meal profile, the patient's insulin profile and observations of the patient's blood glucose concentration. It should be understood, however, that this is merely an example embodiment and that claimed subject matter is not limited in this respect.

Obtaining a patient's physiological parameters as discussed above may assist in characterizing the patient's glycemic response to meals and insulin infusion (e.g., bolus, basal infusion or combinations thereof). These parameters may allow for more effective insulin therapies by, for example, better tuning parameters of a PID control algorithm for computing commands to an insulin infusion pump, setting meal and correction insulin boluses and setting insulin infusion limits to a pump. It should be understood, however, that these are merely examples of how estimates of a patient's physiological parameters may be applied for improving a therapy, and claimed subject matter is not limited in this respect.

FIG. 1 is a block diagram of an example closed-loop glucose control system in accordance with an embodiment. Particular embodiments may include a glucose sensor system 10, a controller 12, an insulin delivery system 14, a glucagon delivery system 13, and a glucose delivery system 15, as shown in FIG. 1. In certain example embodiments, glucose sensor system 10 may generate a sensor signal 16 representative of blood glucose levels 18 in body 20, and it may provide sensor signal 16 to controller 12. Controller 12 may receive sensor signal 16 and generate commands 22 that are communicated to insulin delivery system 14, glucagon delivery system 13, and/or glucose delivery system 15. Insulin delivery system 14 may receive commands 22 and infuse insulin 24 into body 20 in response to commands 22. Likewise, glucagon delivery system 13 may receive commands 22 and infuse glucagon 23 into body 20 in response to commands 22. Similarly, glucose delivery system 15 may receive commands 22 and provide glucose 25 into body 20 in response to commands 22.

Glucose sensor system 10 may include a glucose sensor, sensor electrical components to provide power to a sensor and to generate sensor signal 16, a sensor communication system to carry sensor signal 16 to controller 12, and a sensor system housing for electrical components and a sensor communication system. A glucose sensor may measure blood glucose directly from a blood stream, indirectly via interstitial fluid using e.g. a subcutaneous sensor, some combination thereof, and so forth, just to name a few examples. As used herein, "blood glucose", "measured blood glucose", "blood glucose concentration", "measured blood glucose concentration", and the like may refer to a glucose level, a blood glucose level, a blood glucose concentration, and so forth that has been obtained via any type of glucose sensor. It should be understood, however that using a blood glucose sensor is only one particular technique for obtaining such observations or measurements, and that other techniques, such as measuring blood glucose inform observations of other body fluids (e.g., observations of the presence of glucose in interstitial fluid using a subcutaneous sensor), may be used without deviating from claimed subject matter.

Controller 12 may include electrical components and software to generate commands 22 for insulin delivery system 14, glucagon delivery system 13, and/or glucose delivery system 15 based on sensor signal 16. Controller 12 may also include a controller communication system to receive sensor signal 16 and provide commands 22 to insulin delivery system 14, glucagon delivery system 13, and/or glucose delivery system 15. In particular example implementations, controller 12 may include a user interface and/or operator interface (not shown) comprising a data input device and/or a data output device. Such a data output device may, for example, generate signals to initiate an alarm and/or include a display or printer for showing status of a controller 12 and/or a patient's vital indicators. Such a data input device may comprise dials, buttons, pointing devices, manual switches, alphanumeric keys, a touch-sensitive display, combinations thereof, and/or the like for receiving user and/or operator inputs. Such a data input device may be used for scheduling and/or initiating insulin bolus injections for meals, for example. It should be understood, however, that these are merely examples of input and output devices that may be a part of an operator and/or user interface and that claimed subject matter is not limited in these respects.

Insulin delivery system 14 may include an infusion device and/or an infusion tube to infuse insulin 24 into body 20. Similarly, glucagon delivery system 13 may include an infusion device and/or an infusion tube to infuse glucagon 23 into body 20. Likewise, glucose delivery system 15 may include an infusion device and/or an infusion tube to infuse glucose 25 into body 20. In alternative embodiments, insulin 24, glucagon 23, and/or glucose 25 may be infused into body 20 using a shared infusion tube. In other alternative embodiments, insulin 24, glucagon 23, and/or glucose 25 may be infused using an intravenous system for providing fluids to a patient (e.g., in a hospital or other medical environment). It should be understood, however, that certain example embodiments may include an insulin delivery system 14 without a glucagon delivery system 13 and/or without a glucose delivery system 15.

In particular embodiments, an infusion device (not explicitly identified in FIG. 1) may include infusion electrical components to activate an infusion motor according to commands 22, an infusion communication system to receive commands 22 from controller 12, and an infusion device housing (not shown) to hold the infusion device.

In particular example embodiments, controller 12 may be housed in an infusion device housing, and an infusion communication system may comprise an electrical trace or a wire that carries commands 22 from controller 12 to an infusion device. In alternative embodiments, controller 12 may be housed in a sensor system housing, and a sensor communication system may comprise an electrical trace or a wire that carries sensor signal 16 from sensor electrical components to controller electrical components. In other alternative embodiments, controller 12 may have its own housing or may be included in a supplemental device. In yet other alternative embodiments, controller 12 may be co-located with an infusion device and a sensor system within a single housing. In further alternative embodiments, a sensor, a controller, and/or infusion communication systems may utilize a cable; a wire; a fiber optic line; RF, IR, or ultrasonic transmitters and receivers; combinations thereof; and/or the like instead of electrical traces, just to name a few examples.

Figure 2:
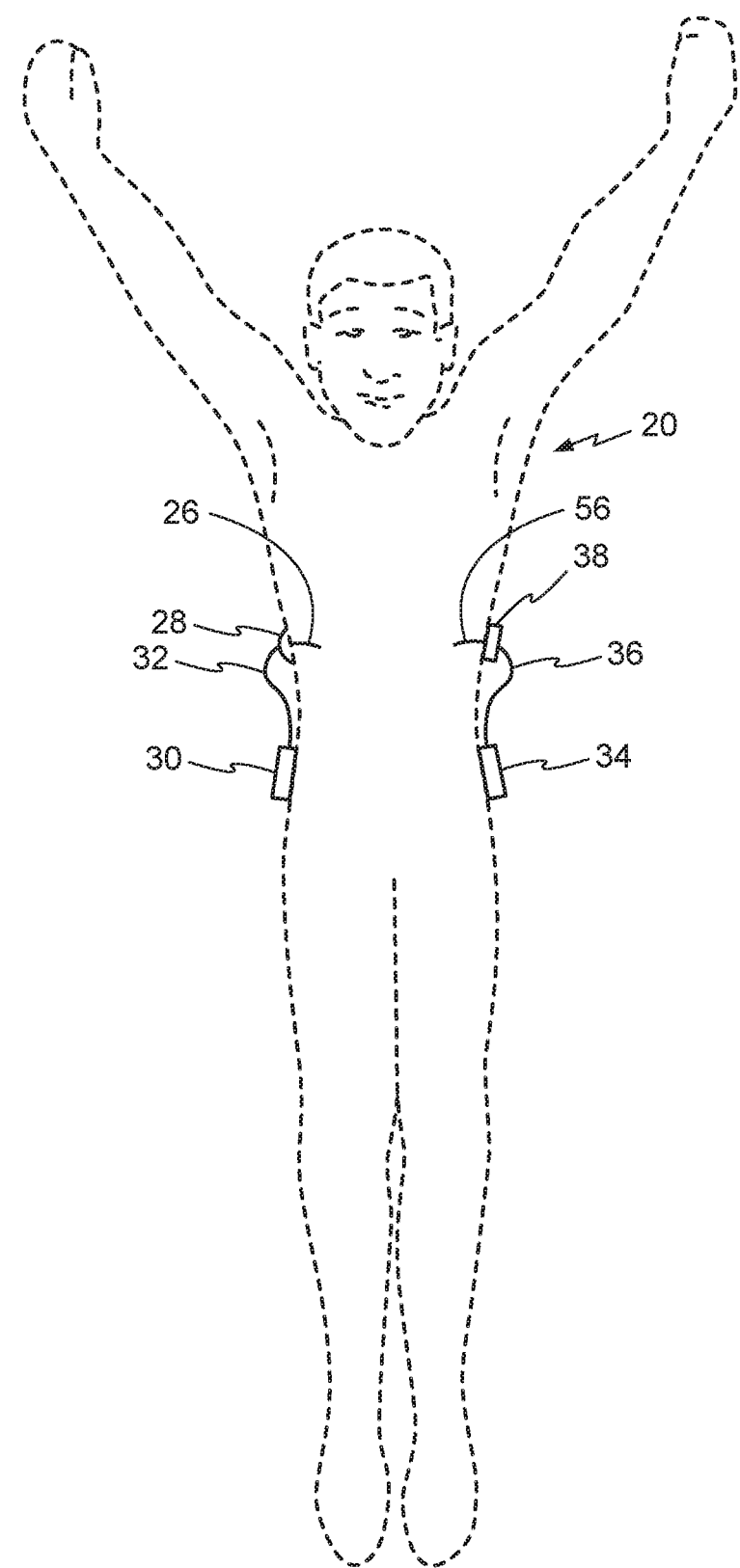
FIG. 2 is a front view of example closed loop hardware located on a body in accordance with an embodiment.
Figures 3A, 3B:
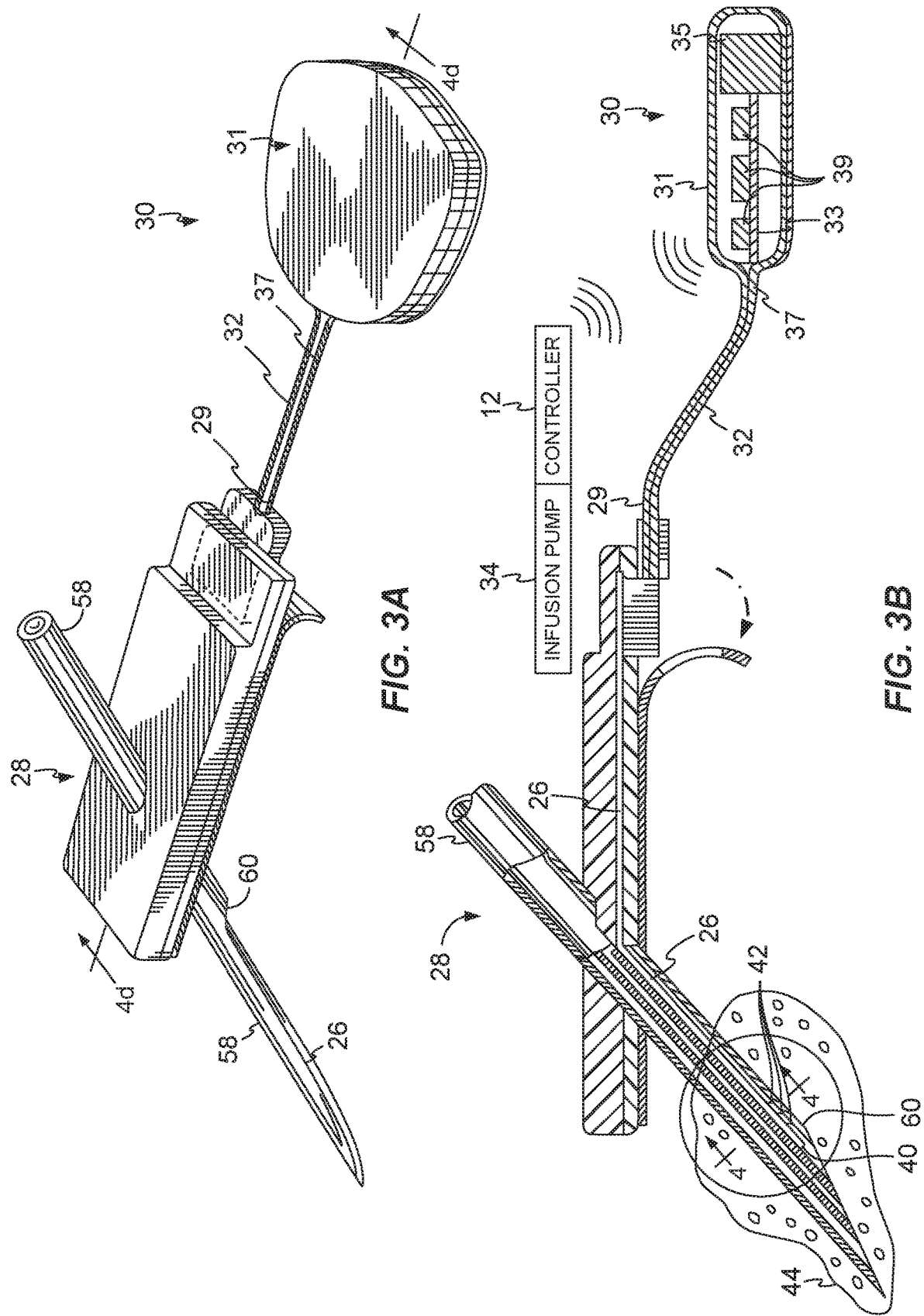
FIG. 3(a) is a perspective view of an example glucose sensor system for use in accordance with an embodiment.
FIG. 3(b) is a side cross-sectional view of a glucose sensor system of FIG. 3(a) for an embodiment.
Figure 3C:
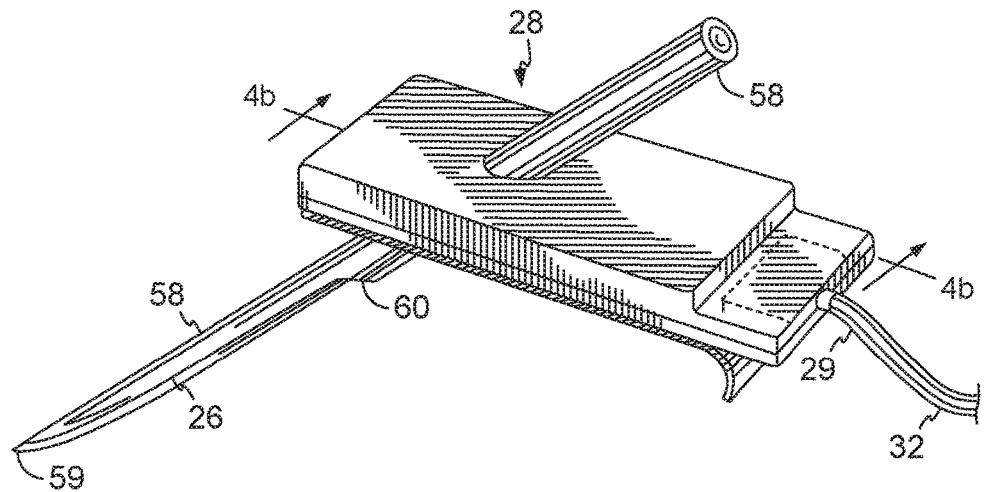
FIG. 3(c) is a perspective view of an example sensor set of a glucose sensor system of FIG. 3(a) for an embodiment.
Figure 3D:
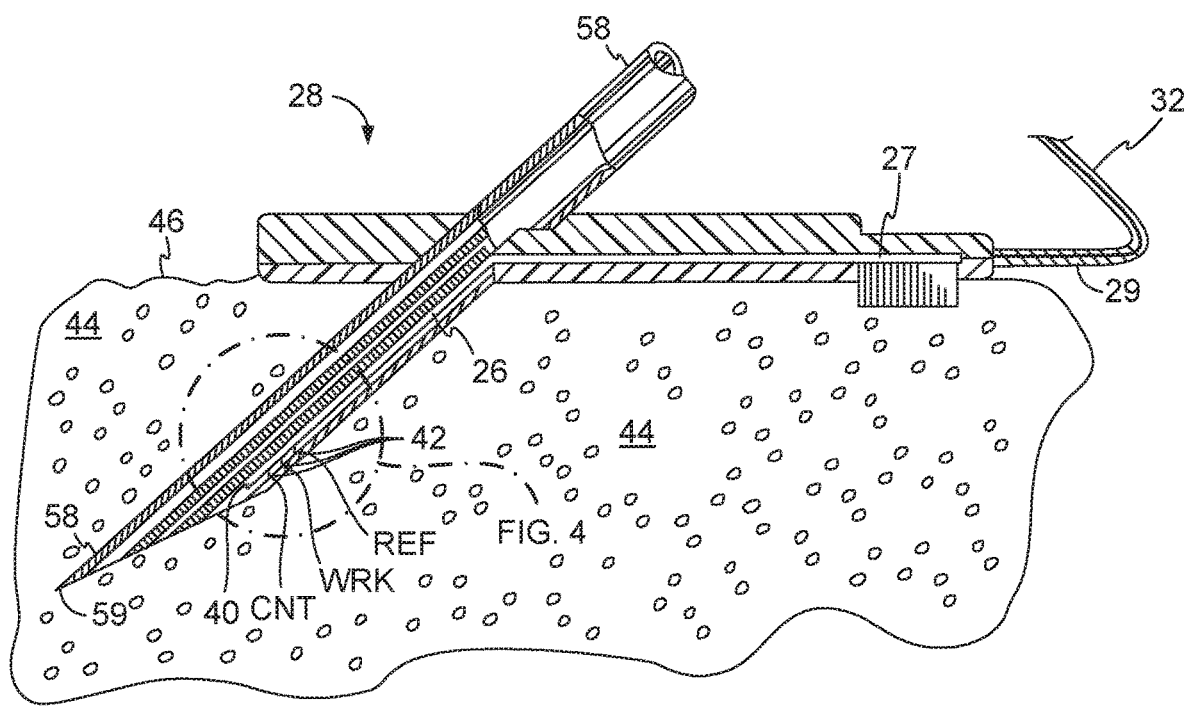
FIG. 3(d) is a side cross-sectional view of a sensor set of FIG. 3(c) for an embodiment.
Figure 4:
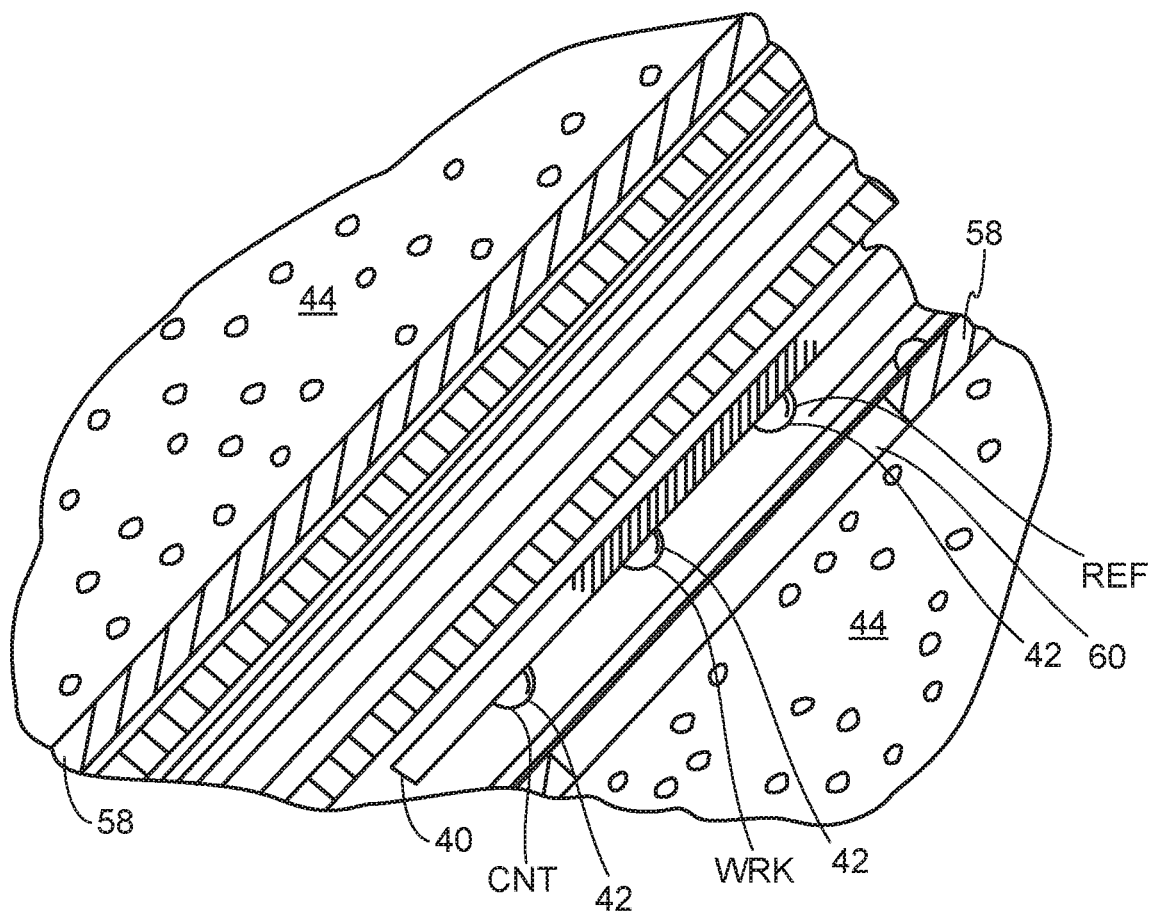
FIG. 4 is a cross sectional view of an example sensing end of a sensor set of FIG. 3(d) for an embodiment.
Figure 5:
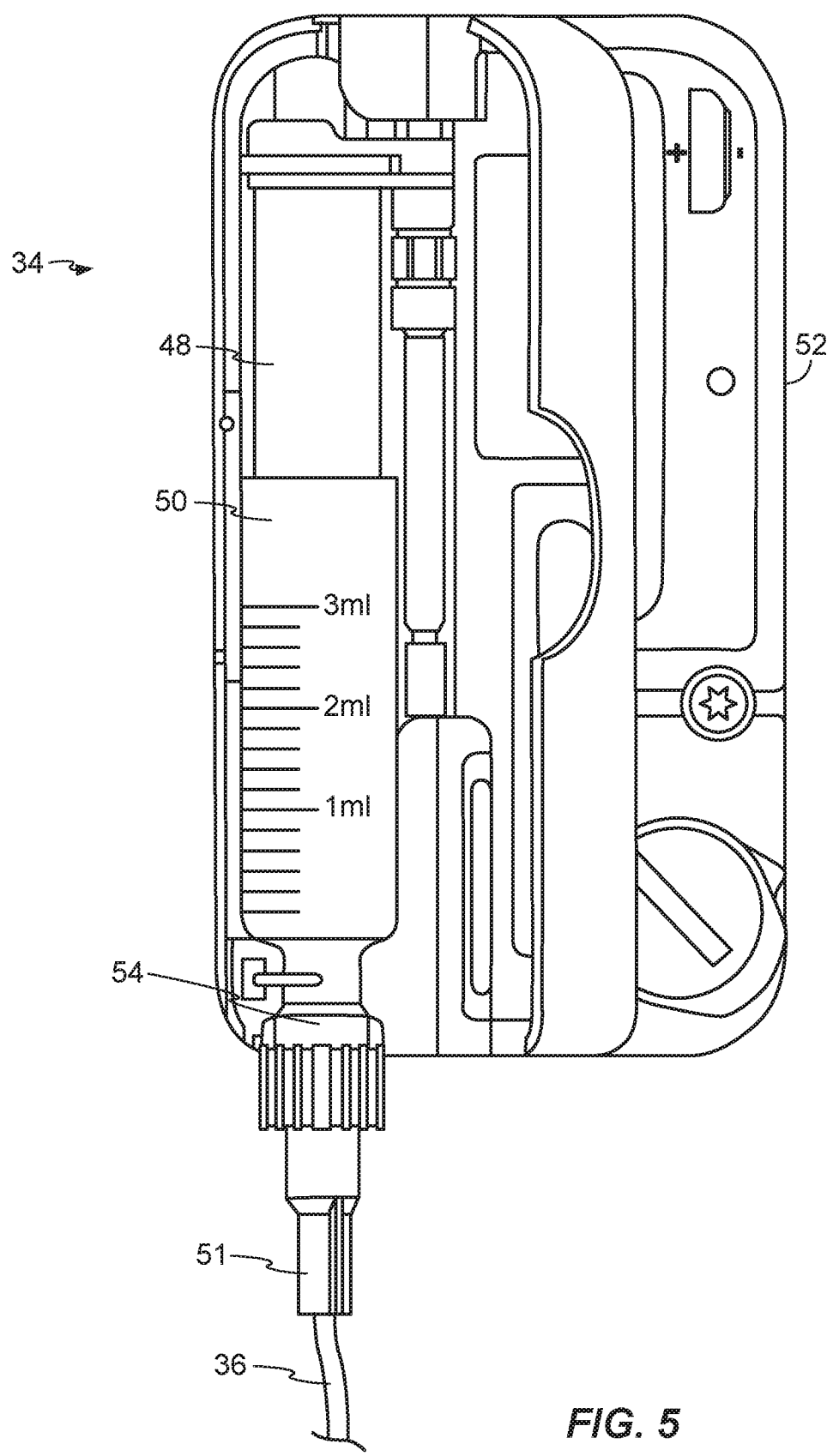
FIG. 5 is a top view of an example infusion device with a reservoir door in an open position, for use according to an embodiment.
Figure 6:
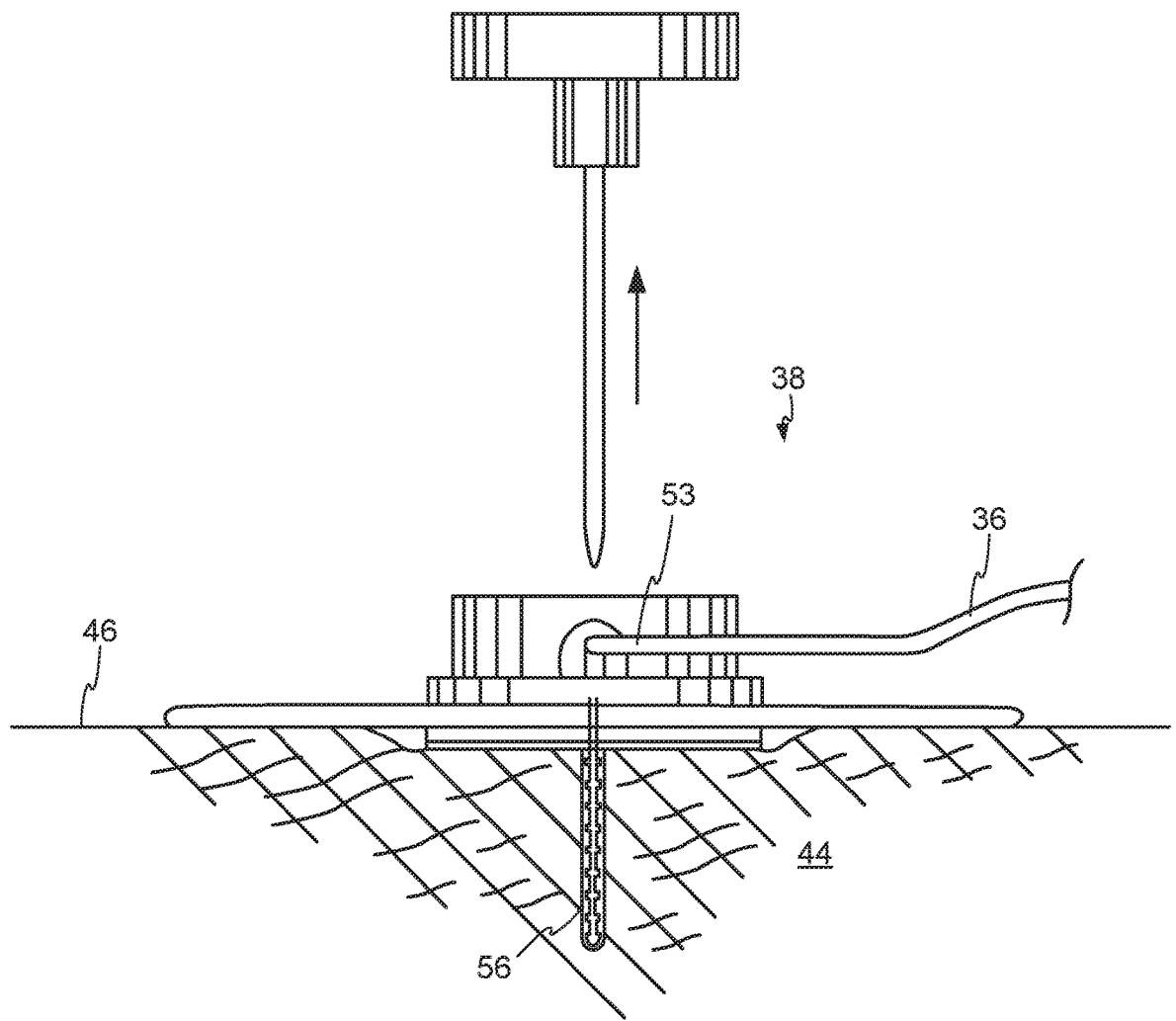
FIG. 6 is a side view of an example infusion set with an insertion needle pulled out, for use according to an embodiment.

FIGS. 2-6 illustrate example glucose control systems in accordance with certain embodiments. Such glucose control systems may be used, for example, in controlling a patient's glucose level about a target range as discussed above. It should be understood, however, that these are merely examples of particular systems that may be used for controlling a patient's glucose level about a target range and that claimed subject matter is not limited in this respect. FIG. 2 is a front view of example closed loop hardware located on a body in accordance with certain embodiments. FIGS. 3(*a*)-3(*d*) and 4 show different views and portions of an example glucose sensor system for use in accordance with certain embodiments. FIG. 5 is a top view of an example infusion device with a reservoir door in an open position in accordance with certain embodiments. FIG. 6 is a side view of an example infusion set with an insertion needle pulled out in accordance with certain embodiments.

Particular example embodiments may include a sensor 26, a sensor set 28, a telemetered characteristic monitor 30, a sensor cable 32, an infusion device 34, an infusion tube 36, and an infusion set 38, any or all of which may be worn on a body 20 of a user or patient, as shown in FIG. 2. As shown in FIGS. 3(*a*) and 3(*b*), telemetered characteristic monitor 30 may include a monitor housing 31 that supports a printed circuit board 33, battery or batteries 35, antenna (not shown), a sensor cable connector (not shown), and so forth. A sensing end 40 of sensor 26 may have exposed electrodes 42 that may be inserted through skin 46 into a subcutaneous tissue 44 of a user's body 20, as shown in FIGS. 3(*d*) and 4. Electrodes 42 may be in contact with interstitial fluid (ISF) that is usually present throughout subcutaneous tissue 44.

Sensor 26 may be held in place by sensor set 28, which may be adhesively secured to a user's skin 46, as shown in FIGS. 3(*c*) and 3(*d*). Sensor set 28 may provide for a connector end 27 of sensor 26 to connect to a first end 29 of sensor cable 32. A second end 37 of sensor cable 32 may connect to monitor housing 31. Batteries 35 that may be included in monitor housing 31 provide power for sensor 26 and electrical components 39 on printed circuit board 33. Electrical components 39 may sample sensor signal 16 (e.g., of FIG. 1) and store digital sensor values (Dsig) in a memory. Digital sensor values Dsig may be periodically transmitted from a memory to controller 12, which may be included in an infusion device.

With reference to FIGS. 2 and 5 (and FIG. 1), a controller 12 may process digital sensor values Dsig and generate commands 22 (e.g., of FIG. 1) for infusion device 34. Infusion device 34 may respond to commands 22 and actuate a plunger 48 that forces insulin 24 (e.g., of FIG. 1) out of a reservoir 50 that is located inside an infusion device 34. Glucose may be infused from a reservoir responsive to commands 22 using a similar and/or analogous device (not shown). In alternative implementations, glucose may be administered to a patient orally.

In particular example embodiments, a connector tip 54 of reservoir 50 may extend through infusion device housing 52, and a first end 51 of infusion tube 36 may be attached to connector tip 54. A second end 53 of infusion tube 36 may connect to infusion set 38 (e.g., of FIGS. 2 and 6). With reference to FIG. 6 (and FIG. 1), insulin 24 (e.g., of FIG. 1) may be forced through infusion tube 36 into infusion set 38 and into body 16 (e.g., of FIG. 1). Infusion set 38 may be adhesively attached to a user's skin 46. As part of infusion set 38, a cannula 56 may extend through skin 46 and terminate in subcutaneous tissue 44 to complete fluid communication between a reservoir 50 (e.g., of FIG. 5) and subcutaneous tissue 44 of a user's body 16.

In example alternative embodiments, as pointed out above, a closed-loop system in particular implementations may be a part of a hospital-based glucose management system. Given that insulin therapy during intensive care has been shown to dramatically improve wound healing and reduce blood stream infections, renal failure, and polyneuropathy mortality, irrespective of whether subjects previously had diabetes (See, e.g., Van den Berghe G. et al. NEJM 345: 1359-67, 2001), particular example implementations may be used in a hospital setting to control a blood glucose level of a patient in intensive care. In such alternative embodiments, because an intravenous (IV) hookup may be implanted into a patient's arm while the patient is in an intensive care setting (e.g., ICU), a closed loop glucose control may be established that piggy-backs off an existing IV connection. Thus, in a hospital or other medical-facility based system, IV catheters that are directly connected to a patient's vascular system for purposes of quickly delivering IV fluids, may also be used to facilitate blood sampling and direct infusion of substances (e.g., insulin, glucose, glucagon, etc.) into an intra-vascular space.

Moreover, glucose sensors may be inserted through an IV line to provide, e.g., real-time glucose levels from the blood stream. Therefore, depending on a type of hospital or other medical-facility based system, such alternative embodiments may not necessarily utilize all of the described system components. Examples of components that may be omitted include, but are not limited to, sensor 26, sensor set 28, telemetered characteristic monitor 30, sensor cable 32, infusion tube 36, infusion set 38, and so forth. Instead, standard blood glucose meters and/or vascular glucose sensors, such as those described in co-pending U.S. Pat. No. 7,833,157; entitled "MULTILUMEN CATHETER", may be used to provide blood glucose values to an infusion pump control, and an existing IV connection may be used to administer insulin to an patient. Other alternative embodiments may also include fewer, more, and/or different components than those that are described herein and/or illustrated in the accompanying Drawings.

Example system and/or environmental delays are described herein. Ideally, a sensor and associated component(s) would be capable of providing a real time, noise-free measurement of a parameter, such as a blood glucose measurement, that a control system is intended to control. However, in real-world implementations, there are typically physiological, chemical, electrical, algorithmic, and/or other sources of time delays that cause a sensor measurement to lag behind an actual present value. Also, as noted herein, such a delay may arise from, for instance, a particular level of noise filtering that is applied to a sensor signal. Such delays and/or time lags in obtaining sensor glucose measurements may ultimately affect closed-loop operation. Accordingly, and as discussed in greater detail below, feedback control mechanisms using various approaches by application of a predicted duration of a blood glucose level being outside of a target range to better address a patient's glycemic health.

Figure 7:
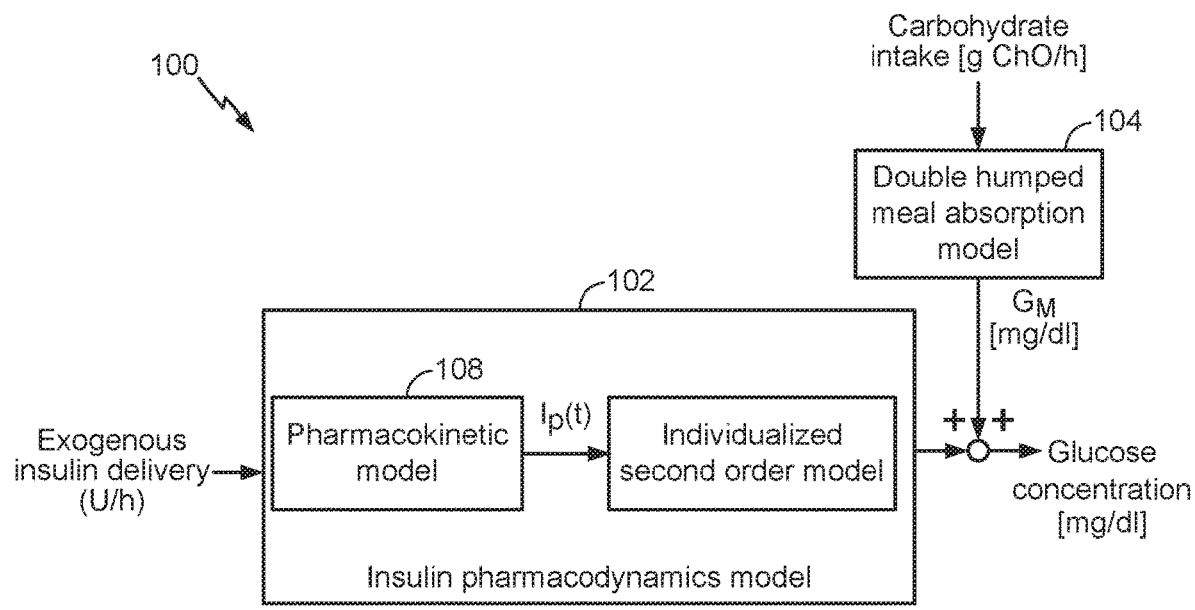
FIG. 7 is a schematic diagram of a system to characterize patient specific parameters for use in control of therapies according to an embodiment.

As pointed out above, embodiments are directed to estimating physiological parameters of a patient to characterize the patient's glycemic response to ingestion of a meal and infusion of insulin. FIG. 7 is a schematic diagram of a system 100 to model a patient's response to an infusion of insulin and ingestion of a meal containing carbohydrates according to an embodiment. Block 102 may model the patient's physiological response to delivery of a known quantity of external or endogenous insulin. Block 104 may model the patient's physiological response to ingestion of a meal comprising a known quantity of carbohydrates. Based, at least in part, on the exogenous insulin delivered at block 102, carbohydrates ingested at block 104 and observations of the patient's blood glucose level, various patient-specific physiological parameters defined in blocks 102 and 104 may be estimated.

According to an embodiment, block 102 may model a patient's physiological response to exogenous insulin based, at least in part, on well-known insulin pharmacokinetics as described in Steil G M, Palerm C C, Kurtz N, et al. The effect of insulin feedback on closed loop glucose control. The Journal of clinical endocrinology and metabolism 2011; 96:1402-8. As pointed out above, an infusion pump may infuse insulin to a patient's subcutaneous tissue in response to a pump command from a controller. Block 102 may model the infusion of exogenous insulin as expressed in a Laplace domain to subcutaneous tissue according to expression (1) as follows:

$$\hat{I}_D(s) = \frac{\hat{I}_{in}}{s}(\exp(-t_1 s) - \exp(-t_2 s)), \quad (1)$$

where $\hat{I}_D$ is insulin intake expressed as a pulse between time $t_1$ and $t_2$ in deviation form ($\hat{I}_D = I_D - I_0$), and $\hat{I}_{in}$ [U/hr] is the insulin intake at time $t_1$ [min] in deviation form ($\hat{I}_{in} = I_{in} - I_0$).

In a particular implementation, block 108 may behave according to a pharmacokinetic model expressing dynamics of plasma insulin ($I_p$) as a function of subcutaneous insulin. Here, according to Steil et al. cited above, plasma insulin ($I_p$) may be expressed in a Laplace domain according to expression (2) as follows:

$$\hat{I}_P(s) = \frac{1}{(50s+1)(70s+1)}(\hat{I}_D + \hat{I}_{P0} s\alpha + dI_{P0}\beta),\quad (2)$$

$$\alpha = 3500; \beta = 120$$

where $\hat{I}_P$ expresses plasma insulin in deviation form ($\hat{I}_P = I_P - I_0$). $\hat{I}_{P0}$ and $dI_{P0}$ are the $\hat{I}_P$ and derivative initial conditions, respectively, and may be estimated based, at least in part, on past delivered insulin.

In a particular implementation, expression (3) below may model effects of a patient's response to insulin infusion on blood glucose concentration as follows:

$$\hat{G}(s) = \frac{1}{(\tau_1 s + 1)\cdot(\tau_2 s + 1)} \quad (3)$$

$$\left(K_I \cdot \hat{I}_P - \frac{1}{(50s+1)(70s+1)}(\hat{G}_0 \cdot \alpha + (\hat{G}_0 \cdot s + d\hat{G}_0)\cdot\beta + \right.$$

$$\left. (\hat{G}_0 \cdot s^2 + d\hat{G}_0 \cdot s)\cdot\chi + (\hat{G}_0 \cdot s^3 + d\hat{G}_0 \cdot s^2)\cdot\delta)\right)$$

$$\alpha = 120 + \tau_1 + \tau_2$$

$$\beta = 3500 + 120\tau_1 + 120\tau_2 + \tau_1\tau_2$$

$$\chi = 3500\tau_1 + 3500\tau_2 + 120\tau_1\tau_2$$

$$\delta = 3500\tau_1\tau_2$$

where $\hat{G}$, $K_I$, $\hat{G}_0$, $d\hat{G}_0$, $\tau_1$, and $\tau_2$ are the blood glucose concentration in deviation form ($\hat{G}=G-G_{out,0}$), the insulin gain, the blood glucose initial conditions in deviation form ($\hat{G}_0 = G_0 - G_{out,0}$) blood glucose derivative initial conditions, and two time constants, respectively.

According to an embodiment, different components of a meal ingested by a patient may increase the patient's blood glucose concentration at different rates. For example, ingestion of a candy bar or highly glycemic fruit (e.g., pineapple or banana) may release a large amount of glucose into the patient's quickly while animal fat may release glucose into the patient's blood more gradually. As such, ingestion of a meal with a mixture of different types of food with different glycemic properties may produce corresponding multiple spikes in blood glucose concentration. In a particular implementation, block 104 may model the release of glucose into a patient's blood according to expression (4) as follows:

$$G_M(s) = \frac{K_{M_1} \cdot M}{(\tau_{M_1} s + 1)^2} \cdot \exp(-D_{meal_1} s) + \frac{K_{M_2} \cdot M}{(\tau_{M_2} s + 1)^2} \cdot \exp(-D_{meal_2} s), \quad (4)$$

where $G_M$ [mg/dL] is a blood glucose concentration increment from meal consumption, M is a profile of a meal including carbohydrate content consumed over a time period, $D_{meal_{1,2}}$ [min] are time delays between the time of the meal intake and the time of the leading edge of a spike in blood glucose concentration, $K_{M_{1,2}}$ are meal response gains, and $\tau_{M_{1,2}}$ are time constants.

Here, expression (4) recognizes two spikes in blood glucose concentration at two different times $D_{meal_{1,2}}$ arising from a faster glycemic component and a slower glycemic component in a "double hump" profile. It should be understood, however, that a meal may be modeled as having three or more of such glycemic components releasing glucose at different times and rates, and that claimed subject matter is not limited in this respect.

According to an embodiment, block 104 may model meal profile M as a time dependent profile having of a beginning of a meal and an end of a meal. In a particular implementation, meal profile M may be represented in a Laplace domain in expression (5) as follows:

$$M = \frac{M_{in}}{s} (\exp(-t_1 s) - \exp(-t_2 s)) \quad (5)$$

where $M_{in}$ is a meal intake [gr·CHO/hr] between a meal start time $t_1$ and a meal end time $\tau_2$ [min]. (In one particular implementation, $M_{in}, t_1$ and $t_2$ may be based, at least in part, on a patient's estimated meal input in gr·CHO. This estimated meal input may be determined, for example, from manual inputs provided by the patient at a controller. Alternatively, values for $M_{in}, t_1$ and $t_2$ may be provided to a controller from a remote server downloaded from a network as part of a patient profile specifying patient specific parameters for glycemic control. If values for $t_1$ and $t_2$ are not indicated, for example, a default meal duration (e.g., 15 min.) may be selected. It should be understood, however that expression (5) is merely one technique that may be used for modeling a meal profile, and claimed subject matter is not limited in this respect.

As pointed out above according to an embodiment, physiological parameters of a patient may characterize the patient's glycemic response to ingestion of a meal and infusion of insulin. These parameters may include, for example, $K_I, \tau_1,$ and $\tau_2$ in expression (3), and $D_{meal_{1,2}}, K_{M_{1,2}}$ and $\tau_{M_{1,2}}$ in expression (4). It should be understood, however, that these are merely examples of physiological parameters which may be estimated to characterize a patient's glycemic response, and claimed subject matter is not limited in this respect. In one particular example, parameters of expressions (3) and (4) may be estimated by, for example relating expressions (3) and (4) to one another and incorporating observations of the patient's blood glucose concentration (e.g., using a continuous glucose monitoring device via a glucose sensor disposed in interstitial fluid as described above, periodic metered blood glucose samples, etc.). Here, expressions (3) and (4) may be related to one another according to expression (6) as follows:

$$G_{out} = G_M(t) + \hat{G}(t) + G_{out,0}, \quad (6)$$

where:

$G_{out,0}$ is an observed fasting blood glucose concentration [mg/dL] at a given basal insulin infusion rate of $I_0$;

$G_{out}$ is the observed blood glucose concentration at time t;

$G_M$ is a blood glucose concentration increment from meal consumption (e.g., from expression (4)); and $\hat{G}$ is the blood glucose concentration in deviation form (e.g., from expression (3)).

Here, by relating expressions (3) and (4) together with multiple observations of blood glucose concentration, parameters $K_I, \tau_1, \tau_2, D_{meal_{1,2}}, K_{M_{1,2}}$ and $\tau_{M_{1,2}}$ may be estimated by applying any one of several "best fit" techniques.

In particular embodiments, Table 1 below summarizes examples of physiological parameters that may be estimated for a patient.

TABLE 1

| Parameter symbol | Description | Estimation method |
|---|---|---|
| $K_I$ | Insulin gain [mg/dL per U/h] | Modified 1800 'rule' |
| $\tau_1$ | Insulin time constant [min] | Daily CGM data |
| $\tau_2$ | Insulin time constant [min] | Daily CGM data |
| $K_{M1}$ | Meal gain [mg/dL per gr CHO/h] | Daily CGM data |
| $K_{M2}$ | Meal gain [mg/dL per gr CHO/h] | Daily CGM data |
| $\tau_{M1}$ | Meal time constant [min] | Daily CGM data |
| $\tau_{M2}$ | Meal time constant [min] | Daily CGM data |
| $D_{meal1}$ | Meal time delay [min] | Daily CGM data |
| $D_{meal2}$ | Meal time delay [min] | Daily CGM data |
| $I_0$ | Insulin reference value [U] | Fasting data |
| $G_{out,0}$ | Glucose reference value | Fasting data |

[mg/dL]

In one particular implementation, various parameters identified above may be estimated in a sequential fashion. For example, a value for $K_I$ may first be estimated based, at least in part, on the so-called "1800 rule," an assessment of a likely drop in a patient's blood glucose level from an amount of exogenous insulin provided. (see, e.g., Kaufman FR. Type 1 diabetes mellitus. Pediatrics in review/American Academy of Pediatrics 2003; 24:291-300) Here, a value for $K_I$ may be estimated according to expression (7) as follows:

$$K_I = -3 \cdot DpU_{1800} \quad (7)$$

$$DpU_{1800} = \frac{1800}{TDI},$$

where:

$DpU_{1800}$ is the drop in mg/dL per unit of insulin may be predicted based, at least in part, on the "1800 rule"; and TDI is a patient's total daily insulin.

Values for $I_0$ and $G_{out,0}$ may be determined from observing a patient's blood glucose concentration over a few fasting periods (e.g., overnight). Here, a basal insulin infusion rate of $I_0$ applied during a fasting period and the patient's blood glucose may be observed as $G_{out,0}$ at the end of that fasting period. With values estimated for $K_I$ according to expression (7) in combination with values estimated for $I_0$ and $G_{out,0}$, values for remaining parameters $\tau_{1,2}$, $K_{M1,2}$, $\tau_{M1,2}$ and $D_{meal1,2}$ may be computed by evaluating observations of blood glucose concentration in response to meals. In one implementation, values for remaining parameters $\tau_{1,2}$ $K_{M1,2}$, $\tau_{M1,2}$, and $D_{meal1,2}$ may be determined to provide a "best fit" according to a minimization of a cost function in expression (8) as follows:

$$\sqrt{\frac{\sum_{k=1}^{k=n}(CGM_k - G_{out,k})^2}{n}}, \quad (8)$$

where $CGM_k$ is a blood glucose concentration observed at time instant k, and $G_{out,k}$ is the model predicted blood glucose at sampling time k In particular implementations, a blood glucose concentration observed at time instant k as $CGM_k$ may be based on blood glucose concentration observed from a continuous glucose monitoring device. However, other techniques to observe a patient's blood glucose concentration, such as metered blood glucose sampling, may be used without deviating from claimed subject matter.

In particular implementations, in computing $G_{out,k}$ for the cost function of expression (8), certain bounds may be placed on values for $\tau_{1,2}$ $K_{M1,2}$, $\tau_{M1,2}$, and $D_{meal1,2}$ In one example implementation, the following boundaries may be established:

$0 < \tau_{1,2} \leq 150[\min]$ $0 < \tau_{M1,2} \leq 90[\min]$ $0 < K_{M1,2} \leq 100\left[\frac{mg/dL}{gr \cdot CHO/hr}\right]$ $0 < D_{meal1} < 10[\min]$ $0 < D_{meal2} < 60[\min]$.

Also, limits may be placed on an absolute relative difference of observed blood glucose concentration $CGM_k$ and initial condition $G_0$ as follows:

$$\left|\frac{CGM_k - G_0(k)}{CGM_k}\right| \leq 0.14$$

Also, limits may be placed on derivatives of initial conditions of blood glucose concentration. For example, derivatives of initial conditions of blood glucose concentrations may be bounded to be no greater than 5.0 mg/dl/min as follows:

$$\left|\frac{dG_0(k)}{dt}\right| \leq 5\left[\frac{mg/dL}{\min}\right].$$

As pointed out above, physiological parameters estimated for a patient may be used to determine an insulin basal rate to be provided to the patient by an insulin infusion pump. Here, with a target blood glucose concentration of 120.0 mg/dL and estimates of $K_I$ and $G_{out,0}$ with corresponding basal value $I_0$, an insulin basal rate $I_{Basal}$ may be determined according to relation (9) as follows:

$$I_{Basal} = \left(I_0 + \frac{120 - G_{out,0}}{K_I}\right).$$

Figure 8:
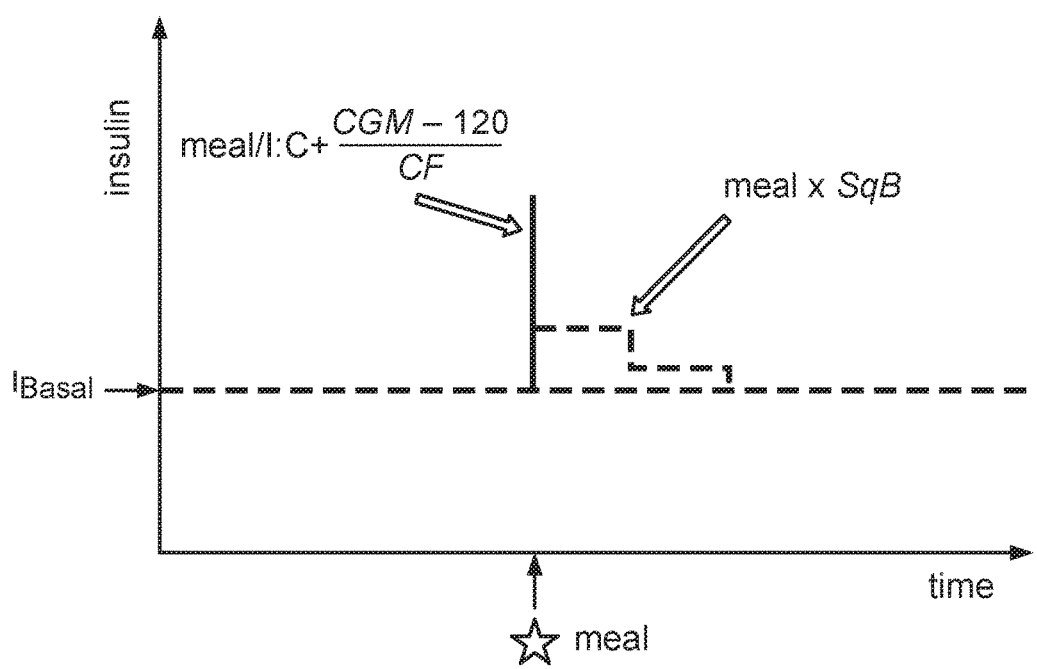
FIG. 8 is a plot illustrating a profile of insulin delivery to a patient according to an embodiment.

While an infusion pump may deliver insulin to a patient at a constant basal rate $I_{Basal}$ under some conditions, the infusion pump may also deliver one or more boluses with or shortly following a meal. In a particular example illustrated in FIG. 8, a profile of insulin delivery indicates a basal rate $I_{Basal}$ along with three boluses including a single impulse bolus provided at mealtime followed by two smaller square boluses. In a particular implementation, a patient's physiological parameters as estimated above may be used to determine the size of insulin boluses to be delivered to the patient during and following meals.

According to an embodiment, components of a post meal bolus may be computed based, at least in part, on a value for above $I_{Basal}$ computed according to expression (9). In one implementation, a post meal bolus may have a profile as a brief change in an insulin basal infusion rate. Expression (10) as follows provides a profile for a post meal bolus including an impulse bolus at a time k at mealtime, followed by a first elevated basal rate from k+1 minute to k+120 minutes, a second elevated base rate from k+121 minutes to k+240 minutes and a third elevated basal rate from k+241 minutes to k+360 minutes:

$$bolus(k) = \frac{Meal}{CR} + correctionbolus$$

$$insulin(k+1:k+120) = PPbasal_1 \cdot Meal + I_{Basal}$$

$$insulin(k+121:k+240) = PPbasal_2 \cdot Meal + I_{Basal}$$

$$insulin(k+241:k+360) = PPbasal_3 \cdot Meal + I_{Basal}$$

$$correctionbolus = \begin{cases} 0 & \frac{CGM_k - BG_{target}}{CF} - IOB < 0 \\ \frac{CGM_k - BG_{target}}{CF} - IOB & \text{otherwise} \end{cases}$$

Where bolus(k) is an insulin impulse [U] given at the discrete moment k, Meal is the meal size in grams of carbohydrates (gr·CHO), CF is a patient's insulin sensitivity $$\left[\frac{mg/dL}{U}\right],$$

CR is a carbohydrate ratio of the meal $$\left[\frac{gr \cdot CHO}{U}\right],$$

PPbasal$_{1,2,3}$ are three values that multiplied by the Meal (gr·CHO) and added to the I$_{Basal}$ produce a six hour post-prandial bolus. IOB [U] is the estimated insulin on board based on the history of delivered insulin. In addition, the post meal bolus of expression (10) may be determined subject to the following constraints:

$$\text{subject to:} \quad (11)$$
$$I:C \in [0, 50]$$
$$CF \in [1, \inf]$$
subject to:
$$0 \le PPbasal_{1,2,3} \le \frac{basal_{max}}{Meal}$$

where a maximum insulin infusion basal rate, basal$_{max}$, may be set by default to 4 [U/h].

A profile for a post meal bolus may be determined so as to balance risks of hyperglycemia and hypoglycemia to the patient. Here $\overline{G}_{pre<0}$ may denote a magnitude of blood glucose predicted to be in a hypoglycemic region while $\overline{G}_{pre\ge0}$ may denote a magnitude of blood glucose predicted to be in a hyperglycemic region. $\overline{G}_{pre<0}$ or $\overline{G}_{pre\ge0}$ for values of PPbasal, CF or I:C—In a particular implementation, PPbasal, CF or I:C may be set/optimized so as to minimize expression (12) below. $\overline{G}_{pre<0}$ may quantify an amount or percentage of time that $G_{out}$ is predicted to be in some predefined hypoglycemia range while $\overline{G}_{pre\ge0}$ may quantify an amount of time that $G_{out}$ is predicted to be out of the predefined hypoglycemia range. In another implementation, values for $G_{out}$ may be predicted for given values of PPbasal, CF or I:C where part of the predicted values of $G_{out}$ may be in a hypoglycemic range, represented by $\overline{G}_{pre<0}$, while remaining values of $G_{out}$ are represented by $\overline{G}_{pre\ge0}$. As pointed out above in a particular implementation, a value for CF, CR, PPbasal may be selected so as to minimize the following cost function of expression (12):

$$\min_{CF,CR,PPbasal} \sqrt{\overline{G}_{pre<0}^2 \times 10 + \overline{G}_{pre\ge0}^2}. \quad (12)$$

An insulin infusion pump may receive commands on discrete intervals determined based, at least in part, on a PID control system. In one particular implementation, a command u(k) to an infusion pump to deliver an amount of insulin may be determined according to expression (10) as follows:

$$u(k) = K_c\left(e(k) + \frac{T}{\tau_I}\sum_{t=0}^{k}e(t') + \tau_D \cdot GSD(k)\right) + \overline{u}, \quad (10)$$

where:
$K_c$, $\tau_I$ and $\tau_D$ are the controller gain, integrator time constant, and differential time constant, respectively;
e(k) is an error between a blood glucose reference measurement and a predetermined set-point or target blood glucose concentration at time instant k;
$\overline{u}$ is the control initial conditions;
GSD(k) an estimated rate of change in blood glucose concentration at time instant k; and T is the sampling time.

According to an embodiment, values for controller gain $K_c$, integrator time constant $\tau_I$ and differential time constant $\tau_D$ may be determined based, at least in part, on one or more physiological parameters estimated for a patient as described above. In one example implementation, values for controller gain $K_c$, integrator time constant $\tau_I$ and differential time constant $\tau_D$ may be determined based, at least in part, on the fourth-order expression (3). Here, exclusive of initial conditions, expression (3) may be characterized by a process p having the form $$\frac{K_I}{(50s+1)(70s+1)\cdot(T_1s+1)\cdot(T_2s+1)}.$$

The fourth-order expression of process p may be approximated as a second-order expression $$\tilde{p} = \frac{K_I}{(\tau_{11}s+1)(\tau_{22}s+1)}.$$

Here, $K_I$, $\tau_{11}$, and $\tau_{22}$ may be equated to obtain estimates for $K_c$, integrator time constant $\tau_I$ and differential time constant $\tau_D$ according to expressions (11), (12) and (13) as follows:

$$K_c = \frac{\tau_{11} + \tau_{22}}{\lambda \cdot K_I} \quad (11)$$

$$\tau_I = \tau_{11} + \tau_{22} \quad (12)$$

$$\tau_D = \frac{\tau_{11} \cdot \tau_{22}}{\tau_{11} + \tau_{22}} \quad (13)$$

where:
$\lambda$ is a tuning parameter that may be set by offline optimization; and
$\tau_{11}$ and $\tau_{22}$ are insulin time constants for the second order expression for $\tilde{p}$.

According to an embodiment, a controller for an insulin infusion pump may set a limit on a maximum amount of insulin to be delivered in an infusion pump command cycle for commands u(k). Here, such a limit Umax may be determined according to relation (15) as follows:

$$U\max = I_0 + \frac{BG_{LBL} - G_{out,0}}{K_I} \quad (15)$$

where $I_0$ is the estimated basal rate defined for a patient, an observed $G_{out,0}$ a fasting blood glucose concentration determined as discussed above, $BG_{LBL}$ mg/dL is a lower buffer limit blood glucose concentration as Umax is approached, and $K_I$, is an insulin gain determined as discussed above. In a particular implementation, Umax may comprise a maximum insulin rate that, if delivered to a patient overnight (or any other fasting period) for a relative long period, the patient's blood glucose would approach eventually to the value of $BG_{LBL}$ (mg/dL). For example, if a patient's estimated $I_0$ is 1.0 U/h, $G_{out,0}$ is 120 mg/dL, the $K_I$, (insulin gain) is −100 mg/dL per U/h, and we may set $BG_{LBL}$ to 70 mg/dL. Then, Umax would be equal to $$1 + \frac{70-120}{-100} = 1.5 \ U/h.$$

Therefore, delivery of 1.5 U/h even under sensor glucose fault without endangering the patient may still be safe because the patient's blood glucose would, theoretically, not fall below 70 mg/dL (or other value defined as $BG_{LBL}$).

Unless specifically stated otherwise, as is apparent from the preceding discussion, it is to be appreciated that throughout this specification discussions utilizing terms such as "processing", "computing", "calculating", "determining", "estimating", "selecting", "identifying", "obtaining", "representing", "receiving", "transmitting", "storing", "analyzing", "associating", "measuring", "detecting", "controlling", "delaying", "initiating", "setting", "delivering", "waiting", "starting", "providing", and so forth may refer to actions, processes, etc. that may be partially or fully performed by a specific apparatus, such as a special purpose computer, special purpose computing apparatus, a similar special purpose electronic computing device, and so forth, just to name a few examples. In the context of this specification, therefore, a special purpose computer or a similar special purpose electronic computing device or apparatus may be capable of manipulating or transforming signals, which are typically represented as physical electronic and/or magnetic quantities within memories, registers, or other information storage devices; transmission devices; display devices of a special purpose computer; or similar special purpose electronic computing device; and so forth, just to name a few examples. In particular example embodiments, such a special purpose computer or similar may comprise one or more processors programmed with instructions to perform one or more specific functions. Accordingly, a special purpose computer may refer to a system or a device that includes an ability to process or store data in the form of signals. Further, unless specifically stated otherwise, a process or method as described herein, with reference to flow diagrams or otherwise, may also be executed or controlled, in whole or in part, by a special purpose computer.

It should be noted that although aspects of the above systems, methods, devices, processes, etc. have been described in particular orders and in particular arrangements, such specific orders and arrangements are merely examples and claimed subject matter is not limited to the orders and arrangements as described. It should also be noted that systems, devices, methods, processes, etc. described herein may be capable of being performed by one or more computing platforms. In addition, instructions that are adapted to realize methods, processes, etc. that are described herein may be capable of being stored on a storage medium as one or more machine readable instructions. If executed, machine readable instructions may enable a computing platform to perform one or more actions. "Storage medium" as referred to herein may relate to media capable of storing information or instructions which may be operated on, or executed by, one or more machines (e.g., that include at least one processor). For example, a storage medium may comprise one or more storage articles and/or devices for storing machine-readable instructions or information. Such storage articles and/or devices may comprise any one of several non-transitory media types including, for example, magnetic, optical, semiconductor, a combination thereof, etc. storage media. By way of further example, one or more computing platforms may be adapted to perform one or more processes, methods, etc. in accordance with claimed subject matter, such as methods, processes, etc. that are described herein. However, these are merely examples relating to a storage medium and a computing platform and claimed subject matter is not limited in these respects.

Although what are presently considered to be example features have been illustrated and described, it will be understood by those skilled in the art that various other modifications may be made, and equivalents may be substituted, without departing from claimed subject matter. Additionally, many modifications may be made to adapt a particular situation to the teachings of claimed subject matter without departing from central concepts that are described herein. Therefore, it is intended that claimed subject matter not be limited to particular examples disclosed, but that such claimed subject matter may also include all aspects falling within the scope of appended claims, and equivalents thereof.

What is claimed is:

1. A method of monitoring and affecting a blood glucose concentration of a patient, the method comprising:
    determining, using a controller, a meal consumption model indicative of a plurality of different blood glucose concentrations of the patient at a plurality of times responsive to ingestion of a meal, wherein the meal comprises a plurality of glycemic components adapted to release glucose in the patient in different amounts at different times;
    determining, using the controller, an insulin model indicative of effects on the blood glucose concentration of the patient responsive to insulin infused in the patient;
    obtaining one or more observations of the blood glucose concentration of the patient;
    computing values for physiological parameters using the controller by relating the meal consumption model and the insulin model with the one or more observations of the blood glucose concentration of the patient, wherein the physiological parameters are specific to the patient and are to model the blood glucose concentration of the patient and comprise a first meal response gain parameter, a second meal response gain parameter, and a plurality of delay parameters; and
    infusing insulin to the patient, using an insulin pump responsive to commands generated by the controller based, at least in part, on the physiological parameters, wherein the physiological parameters are used by the controller to generate the commands to control insulin infusion by the insulin pump.

2. The method of claim 1, wherein the plurality of different glycemic components comprises at least a first glycemic component and a second glycemic component, wherein, if ingested, the first glycemic component being capable of releasing glucose at a first rate and causing a first spike in the blood glucose concentration at a first time, and the second glycemic component being capable of releasing glucose at a second rate and causing a second spike in the blood glucose concentration at a second time.

3. The method of claim 2, wherein the first rate of the first glycemic component is greater than the second rate of the second glycemic component, and wherein the first time of the first glycemic component is prior to the second time of the second glycemic component.

4. The method of claim 1, wherein the insulin model comprises an expression of subcutaneous insulin and an expression of insulin infused.

5. The method of claim 4, wherein the insulin model is defined, at least in part, according to a pharmacokinetic model.

6. The method of claim 1, and further comprising applying at least one of the physiological parameters in determining a meal bolus and one or more correction boluses, wherein the one or more correction boluses comprise a square bolus that is smaller than the meal bolus.

7. The method of claim 1, and further comprising applying at least one of the physiological parameters in determining limits to an amount of the insulin to be specified in an insulin pump command.

8. The method of claim 1, and further comprising applying at least one of the physiological parameters to tune parameters of the controller to determine an amount of the insulin to be infused to the patient on discrete command intervals.

9. The method of claim 1, wherein at least one of the physiological parameters comprises a blood glucose concentration of the patient observed following a fasting period during an infusion of insulin to the patient at a constant basal rate.

10. The method of claim 1, and further comprising computing an insulin infusion basal rate for the patient based, at least in part, on at least one of the physiological parameters.

11. A special purpose computing apparatus, the special purpose computing apparatus comprising:
a memory; and
a processor in communication with the memory, wherein the processor is configured to:
determine a meal consumption model indicative of a plurality of different blood glucose concentrations of a patient at a plurality of times responsive to ingestion of a meal, wherein the meal comprises a plurality of glycemic components adapted to release glucose in the patient in different amounts at different times;
determine an insulin model indicative of effects on the blood glucose concentration of the patient responsive to insulin infused in the patient;
obtain one or more observations of a blood glucose concentration of the patient;
compute values for physiological parameters based, at least in part, on application of the meal consumption model and the insulin model to the one or more observations of the blood glucose concentration of the patient, wherein the physiological parameters to be specific to the patient, to model a blood glucose concentration of the patient, and to comprise a first meal response gain parameter, a second meal response gain parameter and a plurality of delay parameters; and
cause infusion of the insulin to the patient by generating one or more commands to an infusion pump for infusion of the insulin to the patient, the one or more commands based, at least in part, on one or more of the physiological parameters.

12. The special purpose computing apparatus of claim 11, wherein the insulin model to comprise an expression of subcutaneous insulin and an expression of insulin infused.

13. The special purpose computing apparatus of claim 12, wherein the insulin model to be defined, at least in part, according to a pharmacokinetic model.

14. The special purpose computing apparatus of claim 11, wherein the processor further to apply at least one of the physiological parameters to determine a meal bolus and one or more correction boluses, wherein the one or more correction boluses to comprise a square bolus that is smaller than the meal bolus.

15. The special purpose computing apparatus of claim 11, wherein the processor further to apply at least one of the physiological parameters to determine limits to an amount of the insulin to be specified in an insulin pump command.

16. The special purpose computing apparatus of claim 11, wherein the processor further to apply at least one of the physiological parameters to tune parameters of the processor to determine an amount of the insulin to be infused to the patient on discrete command intervals.

17. The special purpose computing apparatus of claim 11, wherein at least one of the physiological parameters to comprise a blood glucose concentration of the patient to be observed following a fasting period during an infusion of insulin to the patient at a constant basal rate.

18. The special purpose computing apparatus of claim 11, wherein the processor further to compute an insulin infusion basal rate for the patient to be based, at least in part, on at least one of the physiological parameters.

19. The special purpose computing apparatus of claim 11, wherein the special purpose computing apparatus further is for use with a glucose sensor, and wherein the special purpose computing apparatus further comprises a continuous glucose monitoring device to provide the one or more observations of the blood glucose concentration of the patient to be based, at least in part, on signals generated by the glucose sensor.

20. An article, the article comprising:
a non-transitory storage medium comprising machine-readable instructions stored thereon which are executable by a special purpose computing apparatus to:
determine a meal consumption model indicative of a plurality of different blood glucose concentrations of a patient at a plurality of times responsive to ingestion of a meal, wherein the meal comprises a plurality of glycemic components adapted to release glucose in the patient in different amounts at different times;
determine an insulin model indicative of effects on the blood glucose concentration of the patient responsive to insulin infused in the patient;
obtain one or more observations of a blood glucose concentration of the patient;
compute values for physiological parameters based, at least in part, on application of the meal consumption model and the insulin model to the one or more observations of the blood glucose concentration of the patient, wherein the physiological parameters to be specific to the patient, to model a blood glucose concentration of the patient, and to comprise a first meal response gain parameter, a second meal response gain parameter and a plurality of delay parameters; and
cause infusion of the insulin to the patient by generating one or more commands to an infusion pump for the infusion of the insulin to the patient, the one or more commands based, at least in part, on one or more of the physiological parameters.

\* \* \* \* \*